(12) United States Patent
Gross

(10) Patent No.: US 9,205,181 B2
(45) Date of Patent: Dec. 8, 2015

(54) INJECTABLE HYDROGEL IMPLANT FOR TREATING GLAUCOMA

(71) Applicant: RAINBOW MEDICAL, LTD., Herzliya (IL)

(72) Inventor: Yossi Gross, Moshav Mazor (IL)

(73) Assignee: RAINBOW MEDICAL, LTD., Herzliya (IL)

( * ) Notice: Subject to any disclaimer, the term of this patent is extended or adjusted under 35 U.S.C. 154(b) by 0 days.

(21) Appl. No.: 14/590,428

(22) Filed: Jan. 6, 2015

(65) Prior Publication Data

US 2015/0190554 A1 Jul. 9, 2015

Related U.S. Application Data

(60) Provisional application No. 61/925,331, filed on Jan. 9, 2014.

(51) Int. Cl.
*A61L 31/14* (2006.01)
*A61L 31/06* (2006.01)

(52) U.S. Cl.
CPC .............. *A61L 31/145* (2013.01); *A61L 31/06* (2013.01); *A61L 2400/06* (2013.01)

(58) Field of Classification Search
CPC ...................................... A61L 31/145
USPC ....................................... 514/547
See application file for complete search history.

(56) References Cited

U.S. PATENT DOCUMENTS

| | | | |
|---|---|---|---|
| 5,486,165 | A | 1/1996 | Stegmann |
| 6,464,724 | B1 | 10/2002 | Lynch et al. |
| 6,485,524 | B2 | 11/2002 | Strecker |
| 6,494,857 | B1 | 12/2002 | Neuhann |
| 7,090,648 | B2 | 8/2006 | Sackner et al. |
| 7,207,980 | B2 | 4/2007 | Christian et al. |
| 2002/0013546 | A1 | 1/2002 | Grieshaber et al. |
| 2002/0013572 | A1 | 1/2002 | Berlin |
| 2002/0103454 | A1 | 8/2002 | Sackner et al. |
| 2004/0193262 | A1 | 9/2004 | Shadduck |
| 2004/0254520 | A1 | 12/2004 | Porteous et al. |
| 2006/0155300 | A1 | 7/2006 | Stamper et al. |
| 2006/0195187 | A1 | 8/2006 | Stegmann et al. |
| 2007/0179471 | A1 | 8/2007 | Christian et al. |
| 2007/0202186 | A1 | 8/2007 | Yamamoto et al. |
| 2007/0287958 | A1 | 12/2007 | McKenzie et al. |
| 2008/0082078 | A1 | 4/2008 | Berlin |
| 2009/0043321 | A1 | 2/2009 | Conston et al. |
| 2009/0247955 | A1 | 10/2009 | Yamamoto et al. |
| 2011/0238133 | A1 | 9/2011 | Gross |

FOREIGN PATENT DOCUMENTS

WO WO/2007/013065 2/2007

OTHER PUBLICATIONS

Cameron B et al., "Circumferential viscodilation of Schlemm's canal with a flexible microcannula during non-penetrating glaucoma surgery," Digital Journal of Ophthalmology, vol. 12, No. 1, Mar. 15, 2006.
Datta A, "Characterization of polyethylene glycol hydrogels for biomedical applications," B.E. University of Pune, India (Aug. 2007).
Farbod, Kambiz, "UV and spontaneously cured polyethylene glycol-based hydrogels for soft and hard tissue scaffolds," Royal Institute of Technology, Apr. 2011.
Flowers BE, "Canaloplasty: Getting the Details Right," Review of Ophthalmology, Mar. 21, 2011.
Glaukos iStent overview, www.online-eye-info.com/istent.html, downloaded Dec. 11, 2013.
Goldberg L, "The Basics of Choosing and Using a Viscoelastic," Ophthalmology Management, Jul. 1, 2007.
Gulrez et al., "Hydrogels: Methods of Preparation, Characterisation and Applications," in Progress in Molecular and Environmental Bioengineering—From Analysis and Modeling to Technology Applications, Prof. Angelo Carpi (Ed.), Aug. 1, 2011.
Healon® Product Information, Sep. 2010.
IScience Interventional release entitled "Interventional Ophthalmology Procedure Indicated for Treatment of Glaucoma" (Aug. 26, 2008).
Luke C et al., "A prospective randomised trial of viscocanalostomy with and without implantation of a reticulated hyaluronic acid implant (SKGEL) in open angle glaucoma," Br J Ophthalmol 87:599-603 (May 2003).
Nguyen KT et al., "Photopolymerizable hydrogels for tissue engineering applications," Biomaterials 23(22):4307-14 (Nov. 2002).
PEGDA Vial Product Data Sheet, Glycosan, Sep. 27, 2011.
Poorsattar BM et al., "The effect of different curing time regimens on immediate postpolymerization color changes of resin composites," J Contemp Dent Pract. 1;13(4):472-5 (Jul. 2012).
Shung AK et al., "Crosslinking characteristics of and cell adhesion to an injectable poly(propylene fumarate-co-ethylene glycol) hydrogel using a water-soluble crosslinking system," Tissue Eng. Apr. 2003;9(2):243-54.
Sun HB and Kawata S, "Two-photon photopolymerization and 3D lithographic microfabrication," Adv. Polym. Sci. 170, 169-273 (2004).
Wang P et al., "Viscoelastic Properties of Polyethylene Glycol (PEG) Boundary Layers near a Solid Substrate" (abstract only), J. Phys. Chem. C, 2009, 113 (2), pp. 729-735 (web publication Dec. 22, 2008).
What is Photoinitiator: Hyaluronan-based Hydrogels by Glycosan, www.glycosan.com/what-is-photoinitiator, downloaded Jan. 5, 2014.

*Primary Examiner* — Taofiq A Solola
(74) *Attorney, Agent, or Firm* — Symbus Law Group, LLC; Clifford D. Hyra

(57) ABSTRACT

A method is provided for increasing the aqueous outflow of fluid through a trabecular meshwork and into a Schlemm's canal of an eye. A liquid hydrogel precursor solution is introduced into the Schlemm's canal, during a medical procedure. The liquid hydrogel precursor solution is crosslinked to form a water-permeable flexible semi-solid hydrogel in the Schlemm's canal, during the medical procedure. The hydrogel is left in the Schlemm's canal upon conclusion of the medical procedure. Other embodiments are also described.

23 Claims, 3 Drawing Sheets

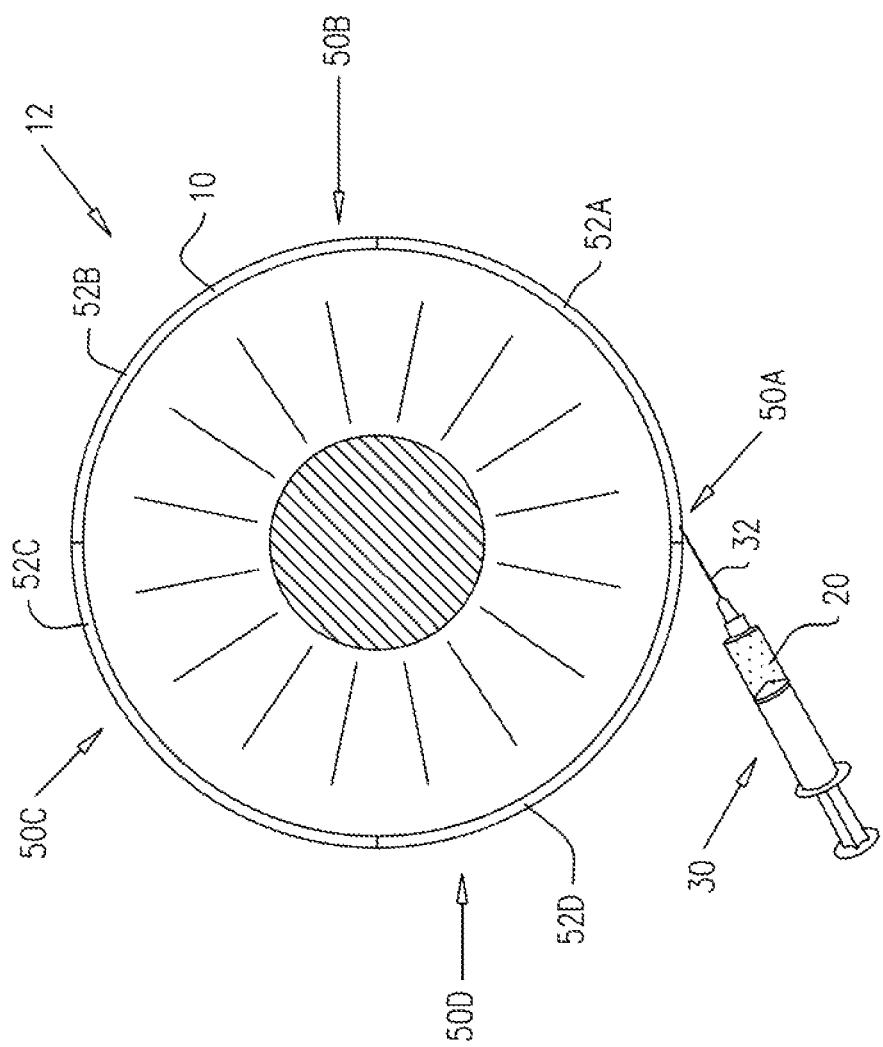

INJECTABLE HYDROGEL IMPLANT FOR TREATING GLAUCOMA

CROSS-REFERENCE TO RELATED APPLICATIONS

The present application claims the benefit of U.S. Provisional Application 61/925,331, filed Jan. 9, 2014, which is assigned to the assignee of the present application and is incorporated herein by reference.

FIELD OF THE APPLICATION

The present invention relates generally to procedures for treating glaucoma.

BACKGROUND OF THE APPLICATION

Glaucoma is a disease which can lead to irreversible loss of vision. A significant risk factor for glaucoma is ocular hypertension, i.e., increased pressure within the eye. Schlemm's canal is a circular channel in the eye that collects aqueous humor from the anterior chamber and delivers it into the bloodstream. On the inside of the canal, nearest to the aqueous humor, it is covered by the trabecular meshwork. If debris builds up, due to infection or injury in the aqueous humor, the canal typically becomes blocked, thereby causing glaucoma.

Canaloplasty, as currently known in the art, is a procedure in which an incision is made into the eye to gain access to Schlemm's canal. A microcatheter circumnavigates the canal around the iris, enlarging the main drainage channel and smaller collector channels through the injection of a sterile, gel-like material called viscoelastic. The catheter is then removed, and a suture is placed within the canal and tightened. By opening the canal, the pressure inside the eye may be relieved.

SUMMARY OF THE APPLICATION

Embodiments of the present invention provide methods for increasing the aqueous outflow of fluid through the trabecular meshwork and into a Schlemm's canal of an eye. The methods are used to treat glaucoma, typically by dilating and/or stretching the canal and/or the trabecular meshwork on a long-term basis. For some applications, the methods apply a force to the inner wall of the canal and the trabecular meshwork, in order to increase fluid permeability of the inner wall of the canal and/or reduce the outflow resistance of the trabecular meshwork, thereby increasing aqueous outflow through the normal trabeculocanalicular pathway. As a result, intraocular pressure is reduced to treat glaucoma.

In some applications of the present invention, the methods comprise:
 introducing a liquid hydrogel precursor solution into the Schlemm's canal, during a medical procedure;
 crosslinking the liquid hydrogel precursor solution to form a water-permeable flexible semi-solid hydrogel in the Schlemm's canal, during the medical procedure; and
 leaving the hydrogel in the Schlemm's canal upon conclusion of the medical procedure.

Because the flexible semi-solid hydrogel is highly water-permeable, it does not interfere with the desired flow in the Schlemm's canal. The hydrogel is left implanted in the canal on a long-term basis, typically indefinitely. The hydrogel thus maintains the patency of the canal on a long-term basis, thereby increasing the aqueous outflow of fluid through the canal. The hydrogel thus serves as an implant. Typically, introducing the liquid hydrogel precursor solution comprises introducing at least 20 mm3 of the liquid hydrogel precursor solution, such as at least 30 mm3, e.g., 36 mm3, for applications in which the entire canal is filled.

In contrast, during some canaloplasty procedures known in the art, a small amount of viscoelastic is injected into the Schlemm's canal after the canal has been surgically opened, such as by creating a scleral flap. The viscoelastic serves as a lubricant for a catheter that is subsequently introduced into the canal. Typically, the viscoelastic does not crosslink in the canal, but is instead absorbed within a few days.

Typically, introducing the liquid hydrogel precursor solution comprises using the liquid hydrogel precursor solution to dilate the Schlemm's canal. Typically, the liquid hydrogel precursor solution is introduced (e.g., injected) at a pressure of at least 25 mmHg, such as at least 30 mmHg. Because the hydrogel precursor solution is a liquid, it generally readily spreads through and fills the Schlemm's canal (or segments thereof, as described hereinbelow), without the need to separately dilate the canal, such as using an implant (e.g., a stent) and/or a viscoelastic. Inserting an implant and/or a viscoelastic generally requires creating a scleral flap and/or advancing a catheter through the entire length of the canal, which can be invasive and time-consuming.

Typically, the liquid hydrogel precursor solution comprises one or more polymerizable monomers and/or one or more polymerizable oligomers. For some applications, the liquid hydrogel precursor solution comprises one of the following materials, or a combination of two or more of the following materials: poly(ethylene glycol) (PEG), such as polyethylene (glycol) diacrylate (PEGDA) or PEG dimethacrylate (PEGDMA); alginate; agarose; chitosan; and/or collagen.

For some applications, the liquid hydrogel precursor solution is crosslinked by applying radiation to the liquid hydrogel precursor solution in the Schlemm's canal (i.e., by photopolymerization, also known in the art as radiation curing). For example, the radiation may comprise ultraviolet (UV) radiation, infrared (IR) radiation (such as near-infrared (NIR) radiation), or electron-beam (EB) radiation. Alternatively, for example, the liquid hydrogel precursor solution is crosslinked by two-photon excitation.

For some applications, the liquid hydrogel precursor solution further comprises a photoinitiator. For some applications, the radiation interacts with the light-sensitive photoinitiator to create free radicals that initiate polymerization to form the crosslinked hydrogel. Such photopolymerization typically has a fast curing rate (between less than a second to a few minutes) at physiological temperatures, and produces minimal heat.

For some applications, the liquid hydrogel precursor solution is chemically crosslinked in the Schlemm's canal (typically without applying radiation to the liquid hydrogel precursor solution, other than any ambient light to which the solution may be exposed). For example, the liquid hydrogel precursor solution may be chemically crosslinked using a crosslinking agent, as known in the hydrogel art, which is introduced into the Schlemm's canal before, during, or after introducing the liquid hydrogel precursor solution into the canal.

For some applications, crosslinking the liquid hydrogel precursor solution comprises observing a change in color of the liquid hydrogel precursor solution that is indicative of a level of crosslinking of the liquid hydrogel precursor solution, and terminating the crosslinking in response to the change in color. In other words, the change in color is used as feedback to monitor the level of crosslinking (and formation of hydrogel).

As mentioned above, because the hydrogel precursor solution is liquid, it generally readily spreads through and fills the Schlemm's canal. Thus, for some medical procedures, in which the precursor solution fills the entire canal, it is sufficient to introduce the liquid hydrogel precursor solution at a single site of the Schlemm's canal. For some medical procedures in which introducing the hydrogel precursor solution at a single site of the canal is insufficient to fill the entire canal, the surgeon introduces the hydrogel precursor solution into a plurality of segments of the Schlemm's canal at a respective plurality of sites along the Schlemm's canal.

In some applications of the present invention, a glaucoma medication is mixed with the liquid hydrogel precursor solution, typically before introducing the liquid hydrogel precursor solution into the Schlemm's canal, or, alternatively, in the canal by separate introduction. The hydrogel is configured for long-term sustained release of the medication into the eye. Some hydrogels, such as those that comprise PEG, are well-suited for long-term sustained release. The glaucoma medication may comprise any topical ocular medication known in the art or developed in the future. These applications thus provide a dual-mode therapy modality for glaucoma.

There is therefore provided, in accordance with an application of the present invention, a method for increasing the aqueous outflow of fluid through a trabecular meshwork and into a Schlemm's canal of an eye, the method including:

introducing a liquid hydrogel precursor solution into the Schlemm's canal, during a medical procedure;

crosslinking the liquid hydrogel precursor solution to form a water-permeable flexible semi-solid hydrogel in the Schlemm's canal, during the medical procedure; and leaving the hydrogel in the Schlemm's canal upon conclusion of the medical procedure.

For some applications, introducing the liquid hydrogel precursor solution includes using the liquid hydrogel precursor solution to dilate the Schlemm's canal. For some applications, introducing the liquid hydrogel precursor solution includes applying fluid pressure to a wall of the Schlemm's canal. For some applications, introducing the liquid hydrogel precursor solution includes applying the fluid pressure to the wall of the Schlemm's canal along at least 50% of a circumference of the Schlemm's canal. For some applications, introducing the liquid hydrogel precursor solution includes filling the Schlemm's canal along at least 50% of a circumference of the Schlemm's canal. For some applications, introducing and crosslinking the liquid hydrogel precursor solution and leaving the hydrogel in the Schlemm's canal includes introducing and crosslinking the liquid hydrogel precursor solution to form the hydrogel along at least 50% of a circumference of the Schlemm's canal.

For some applications, introducing the liquid hydrogel precursor solution includes introducing at least 20 mm3 of the liquid hydrogel precursor solution. For some applications, introducing the liquid hydrogel precursor solution includes introducing the liquid hydrogel precursor solution at a pressure of at least 25 mmHg.

For some applications, the liquid hydrogel precursor solution includes poly(ethylene glycol) (PEG). For example, the PEG may include polyethylene (glycol) diacrylate (PEGDA) PEG dimethacrylate (PEG-DMA), and/or ammonium persulfate (APS). Alternatively or additionally, for some applications, the liquid precursor solution includes a material selected from the group consisting of: alginate, agarose, chitosan, and collagen.

For some applications, the liquid hydrogel precursor solution is viscous, and introducing includes introducing the viscous liquid hydrogel precursor solution.

For some applications, crosslinking the liquid hydrogel precursor solution includes applying radiation to the liquid hydrogel precursor solution in the Schlemm's canal. For some applications, applying the radiation includes applying the radiation through sclera of the eye. For some applications, applying the radiation includes applying the radiation through sclera of the eye. For some applications, applying the radiation includes applying infrared (IR) radiation, ultraviolet (UV) radiation, and/or electron-beam (EB) radiation to the liquid hydrogel precursor solution in the Schlemm's canal. For some applications, applying the radiation includes crosslinking the liquid hydrogel precursor solution by two-photon excitation. For some applications, the liquid hydrogel precursor solution includes at least two components, one of which components includes a photoinitiator. For some applications, introducing the liquid hydrogel precursor solution includes introducing one of the two components into the Schlemm's canal, and thereafter introducing the other of the two components into the Schlemm's canal. For some applications, introducing the liquid hydrogel precursor solution includes mixing the two components while introducing them into the Schlemm's canal. For some applications, the method further includes, before introducing the liquid hydrogel precursor solution, preparing the liquid hydrogel precursor solution by mixing at least the two components; and introducing the liquid hydrogel precursor solution includes introducing the liquid hydrogel precursor solution into the Schlemm's canal within three hours of mixing.

For some applications, crosslinking the liquid hydrogel precursor solution includes chemically crosslinking the liquid hydrogel precursor solution. For some applications, chemically crosslinking the liquid hydrogel precursor includes introducing a crosslinking agent into the Schlemm's canal, such as ammonium persulfate (APS).

For some applications, the method further includes, before introducing the liquid hydrogel precursor solution, preparing the liquid hydrogel precursor solution by mixing at least two components; and introducing the liquid hydrogel precursor solution includes introducing the liquid hydrogel precursor solution into the Schlemm's canal within three hours of mixing. For some applications, at least one of the components includes a crosslinking agent.

For some applications, crosslinking the liquid hydrogel precursor solution includes: observing a change in color of the liquid hydrogel precursor solution that is indicative of a level of crosslinking of the liquid hydrogel precursor solution; and terminating the crosslinking in response to the change in color.

For some applications, leaving the hydrogel in the Schlemm's canal upon conclusion of the medical procedure includes leaving the hydrogel in the Schlemm's canal for at least one month.

For some applications:

introducing includes inserting a needle into the Schlemm's canal and introducing the liquid hydrogel precursor solution through the needle, the method further includes removing the needle from the Schlemm's canal after introducing the liquid hydrogel precursor solution through the needle, and leaving the hydrogel in the Schlemm's canal upon conclusion of the medical procedure further includes leaving the hydrogel in the Schlemm's canal after removing the needle from the Schlemm's canal.

For some applications, the method further includes, upon the conclusion of the medical procedure, not leaving any solid elements in the Schlemm's canal. Alternatively or additionally, for some applications, the method further includes, upon the conclusion of the medical procedure, not leaving, in the Schlemm's canal, any elements placed into the Schlemm's canal during the medical procedure that apply any force to the Schlemm's canal, other than the hydrogel.

For some applications, introducing include injecting the liquid hydrogel precursor solution.

For some applications, introducing includes introducing the liquid hydrogel precursor solution at a single site of the Schlemm's canal.

For some applications, introducing includes introducing the liquid hydrogel precursor solution into a plurality of segments of the Schlemm's canal at a respective plurality of sites along the Schlemm's canal.

For some applications, introducing the liquid hydrogel precursor solution includes introducing at least 20 mm3 of the liquid hydrogel precursor solution.

For some applications, introducing the liquid hydrogel precursor solution includes introducing the liquid hydrogel precursor solution at a pressure of at least 25 mmHg.

For some applications, the medical procedure is a first medical procedure, and the method further includes:
  assessing a pressure in the eye at least 1 week following the first medical procedure; and
  in response to assessing the pressure:
    introducing a liquid hydrogel precursor solution into the Schlemm's canal, during a second medical procedure;
    crosslinking the liquid hydrogel precursor solution to form a water-permeable flexible semi-solid hydrogel in the Schlemm's canal, during the second medical procedure; and
    leaving the hydrogel in the Schlemm's canal upon conclusion of the second medical procedure.

For example, introducing the liquid hydrogel precursor solution during the first medical procedure may include filling less than 75% of the Schlemm's canal with the liquid hydrogel precursor solution. Correspondingly, introducing the liquid hydrogel precursor solution during the second medical procedure may include filling at least part of a portion of the Schlemm's canal that was not filled with liquid hydrogel precursor solution during the first medical procedure.

For some applications, the medical procedure is a first medical procedure, and the method further includes:
  assessing a pressure in the eye at least 1 week following the first medical procedure; and
  in response to assessing the pressure:
    introducing a second liquid hydrogel precursor solution into the Schlemm's canal, during a second medical procedure;
    crosslinking the second liquid hydrogel precursor solution to form a second water-permeable flexible semi-solid hydrogel in the Schlemm's canal, during the second medical procedure; and
    leaving the second hydrogel in the Schlemm's canal upon conclusion of the second medical procedure.

For some applications, introducing the first liquid hydrogel precursor solution during the first medical procedure includes filling less than 75% of the Schlemm's canal with the first liquid hydrogel precursor solution. For some applications, introducing the second liquid hydrogel precursor solution during the second medical procedure includes filling at least part of a portion of the Schlemm's canal that was not filled with the first liquid hydrogel precursor solution during the first medical procedure.

For some applications:
  the medical procedure is a first test medical procedure,
  the hydrogel is a first test hydrogel,
  the liquid hydrogel precursor solution is a first test liquid hydrogel precursor solution that is configured such that the first test hydrogel degrades less than four months after the conclusion of the first test medical procedure, and
  the method further includes:
    at least one month after the conclusion of the first test medical procedure, assessing an effectiveness of the first test hydrogel at increasing the aqueous outflow of fluid; and
    if the first test hydrogel is effective at increasing the aqueous outflow of fluid:
      introducing a second liquid hydrogel precursor solution into the Schlemm's canal, during a second medical procedure;
      crosslinking the second liquid hydrogel precursor solution to form a second water-permeable flexible semi-solid hydrogel in the Schlemm's canal, during the second medical procedure; and
      leaving the second hydrogel in the Schlemm's canal upon conclusion of the second medical procedure,
      wherein the second liquid hydrogel precursor solution is configured such that the second hydrogel does not degrade until at least two years after the conclusion of the second medical procedure.

For some applications, the second liquid hydrogel precursor solution includes ammonium persulfate (APS)

There is further provided, in accordance with an application of the present invention, a method for increasing the aqueous outflow of fluid through a trabecular meshwork and into a Schlemm's canal of an eye, the method including:
  introducing a first liquid hydrogel precursor solution into the Schlemm's canal, during a medical procedure;
  introducing a second liquid hydrogel precursor solution into the Schlemm's canal, during the medical procedure, wherein the first and the second liquid hydrogel precursor solutions are different from each other, and are configured to together crosslink to form a water-permeable flexible semi-solid hydrogel in the Schlemm's canal, during the medical procedure; and
  leaving the hydrogel in the Schlemm's canal upon conclusion of the medical procedure.

For some applications, the first and the second liquid hydrogel precursor solutions are configured to together chemically crosslink to the form the hydrogel in the Schlemm's canal.

For some applications, introducing the first and the second liquid initiated solutions includes using at least one of the first and the second liquid initiated solutions to dilate the Schlemm's canal. For some applications, introducing the first and the second liquid hydrogel precursor solutions includes applying fluid pressure to a wall of the Schlemm's canal. For some applications, introducing the first and the second liquid hydrogel precursor solutions includes applying the fluid pressure to the wall of the Schlemm's canal along at least 50% of a circumference of the Schlemm's canal. For some applications, introducing the first and the second liquid hydrogel precursor solutions includes filling the Schlemm's canal along at least 50% of a circumference of the Schlemm's canal. For some applications, introducing the first and the second liquid hydrogel precursor solutions and leaving the hydrogel in the Schlemm's canal includes introducing the first and the second liquid hydrogel precursor solutions to form the hydrogel along at least 50% of a circumference of the Schlemm's canal.

For some applications, introducing the first and the second liquid hydrogel precursor solutions includes introducing at least 20 mm3 of the first and the second liquid hydrogel precursor solutions in aggregate. For some applications, introducing the first and the second liquid hydrogel precursor solutions includes introducing at least one of the first and the second liquid hydrogel precursors solution at a pressure of at least 25 mmHg. For some applications, one of the first and the second liquid hydrogel precursor solutions includes ammonium persulfate (APS). For some applications, the other of the first and the second liquid hydrogel precursor solutions includes poly(ethylene glycol) (PEG).

For some applications, introducing the first and the second liquid hydrogel precursor solutions includes introducing the first liquid hydrogel precursor solution into the Schlemm's canal, and thereafter introducing the second liquid hydrogel precursor solution into the Schlemm's canal.

For some applications, introducing the first and the second liquid hydrogel precursor solutions includes mixing the first and the second liquid hydrogel precursor solutions while introducing them into the Schlemm's canal.

For some applications, leaving the hydrogel in the Schlemm's canal upon conclusion of the medical procedure includes leaving the hydrogel in the Schlemm's canal for at least one month.

For some applications:
introducing the first liquid hydrogel precursor solution includes inserting a first needle into the Schlemm's canal and introducing the first liquid hydrogel precursor solution through the first needle,
the method further includes removing the first needle from the Schlemm's canal after introducing the first liquid hydrogel precursor solution through the first needle,
introducing the second liquid hydrogel precursor solution includes inserting a second needle into the Schlemm's canal and introducing the second liquid hydrogel precursor solution through the second needle,
the method further includes removing the second needle from the Schlemm's canal after introducing the second liquid hydrogel precursor solution through the second needle, and
leaving the hydrogel in the Schlemm's canal upon conclusion of the medical procedure further includes leaving the hydrogel in the Schlemm's canal after removing the first and the second needles from the Schlemm's canal.

For some applications, the method further includes, upon the conclusion of the medical procedure, not leaving any solid elements in the Schlemm's canal.

For some applications, the method further includes, upon the conclusion of the medical procedure, not leaving, in the Schlemm's canal, any elements placed into the Schlemm's canal during the medical procedure that apply any force to the Schlemm's canal, other than the hydrogel.

For some applications, introducing include injecting the first and the second liquid hydrogel precursor solution.

For some applications, introducing includes introducing the first and the second liquid hydrogel precursor solutions into a plurality of segments of the Schlemm's canal at a respective plurality of sites along the Schlemm's canal.

For some applications, introducing the first and the second liquid hydrogel precursor solutions includes introducing at least 20 mm3 of the first and the second liquid hydrogel precursor solutions in aggregate.

For some applications, introducing the first and the second liquid hydrogel precursor solutions includes introducing at least one of the first and the second liquid hydrogel precursors solution at a pressure of at least 25 mmHg.

For some applications, the medical procedure is a first medical procedure, and the method further includes:
assessing a pressure in the eye at least 1 week following the first medical procedure; and
in response to assessing the pressure:
introducing a third liquid hydrogel precursor solution into the Schlemm's canal, during a second medical procedure;
introducing a fourth liquid hydrogel precursor solution into the Schlemm's canal, during the second medical procedure, wherein the second and the third liquid hydrogel precursor solutions are different from each other, and are configured to together crosslink to form a second water-permeable flexible semi-solid hydrogel in the Schlemm's canal, during the second medical procedure; and
leaving the second hydrogel in the Schlemm's canal upon conclusion of the second medical procedure.

For some applications, introducing the first and the second liquid hydrogel precursor solutions during the first medical procedure includes filling less than 75% of the Schlemm's canal with the first and the second liquid hydrogel precursor solutions. For some applications, introducing the third and the fourth liquid hydrogel precursor solutions during the second medical procedure includes filling at least part of a portion of the Schlemm's canal that was not filled with the first and the second liquid hydrogel precursor solutions during the first medical procedure.

For some applications:
the medical procedure is a first test medical procedure,
the hydrogel is a first test hydrogel,
the first and the second liquid hydrogel precursor solutions are configured such that the first test hydrogel degrades less than four months after the conclusion of the first test medical procedure, and
the method further includes:
at least one month after the conclusion of the first test medical procedure, assessing an effectiveness of the first test hydrogel at increasing the aqueous outflow of fluid; and
if the first test hydrogel is effective at increasing the aqueous outflow of fluid:
introducing a third liquid hydrogel precursor solution into the Schlemm's canal, during a second medical procedure;
introducing a fourth liquid hydrogel precursor solution into the Schlemm's canal, during the second medical procedure, the third and the fourth liquid hydrogel precursor solutions are different from each other, and are configured to together crosslink to form a second water-permeable flexible semi-solid hydrogel in the Schlemm's canal, during the second medical procedure; and
leaving the second hydrogel in the Schlemm's canal upon conclusion of the second medical procedure,
wherein the third and the fourth liquid hydrogel precursor solutions are configured such that the second hydrogel does not degrade until at least two years after the conclusion of the second medical procedure.

For some applications, one of the third and the fourth liquid hydrogel precursor solutions includes ammonium persulfate (APS).

There is still further provided, in accordance with an application of the present invention, a method for increasing the aqueous outflow of fluid through a trabecular meshwork and into a Schlemm's canal of an eye, the method including:
preparing a liquid initiated solution by mixing at least first and second components;
during a medical procedure, facilitating chemical transformation of the liquid initiated solution to a flexible semi-solid in the Schlemm's canal, by introducing the liquid initiated solution into the Schlemm's canal within three hours of mixing; and
leaving the flexible semi-solid in the Schlemm's canal upon conclusion of the medical procedure.

For some applications, the flexible semi-solid is a flexible semi-solid hydrogel, and facilitating the chemical transformation of the liquid initiated solution to the flexible semi-solid includes facilitating chemical crosslinking of the liquid initiated solution to form the flexible semi-solid hydrogel in the Schlemm's canal, by introducing the liquid initiated solution into the Schlemm's canal within three hours of mixing.

For some applications, the flexible semi-solid is a flexible semi-solid hydrogel, and facilitating the chemical transformation of the liquid initiated solution to the flexible semi-solid includes facilitating chemical polymerization of the liquid initiated solution to form the flexible semi-solid hydrogel in the Schlemm's canal, by introducing the liquid initiated solution into the Schlemm's canal within three hours of mixing.

For some applications, introducing the liquid initiated solution includes using the liquid initiated solution to dilate the Schlemm's canal. For some applications, introducing the liquid initiated solution includes applying fluid pressure to a wall of the Schlemm's canal. For some applications, introducing the liquid initiated solution includes applying the fluid pressure to the wall of the Schlemm's canal along at least 50% of a circumference of the Schlemm's canal. For some applications, introducing the liquid initiated solution includes filling the Schlemm's canal along at least 50% of a circumference of the Schlemm's canal. For some applications, facilitating the chemical transformation includes facilitating the chemical transformation of the liquid initiated solution to form the flexible semi-solid along at least 50% of a circumference of the Schlemm's canal.

For some applications, introducing the liquid initiated solution includes introducing at least 20 mm3 of the liquid initiated solution. For some applications, introducing the liquid initiated solution includes introducing the liquid initiated solution at a pressure of at least 25 mmHg.

For some applications, the first component includes a liquid hydrogel precursor solution, and the second component includes a crosslinking agent. For some applications, the liquid hydrogel precursor solution includes poly(ethylene glycol) (PEG). For example, the PEG includes polyethylene (glycol) diacrylate (PEGDA) and/or PEG dimethacrylate (PEG-DMA). For some applications, the crosslinking agent includes ammonium persulfate (APS). Alternatively or additionally, for some applications, the liquid precursor solution includes a material selected from the group consisting of: alginate, agarose, chitosan, and collagen.

For some applications, the first component includes a first liquid hydrogel precursor solution, and the second component includes a second liquid hydrogel precursor solution.

For some applications, the liquid initiated solution is viscous, and introducing includes introducing the viscous liquid initiated solution.

For some applications, leaving the hydrogel in the Schlemm's canal upon conclusion of the medical procedure includes leaving the hydrogel in the Schlemm's canal for at least one month.

For some applications:
introducing includes inserting a needle into the Schlemm's canal and introducing the liquid initiated solution through the needle,
the method further includes removing the needle from the Schlemm's canal after introducing the liquid initiated solution through the needle, and
leaving the hydrogel in the Schlemm's canal upon conclusion of the medical procedure further includes leaving the hydrogel in the Schlemm's canal after removing the needle from the Schlemm's canal.

For some applications, the method further includes, upon the conclusion of the medical procedure, not leaving any solid elements in the Schlemm's canal. Alternatively or additionally, for some applications, the method further includes, upon the conclusion of the medical procedure, not leaving, in the Schlemm's canal, any elements placed into the Schlemm's canal during the medical procedure that apply any force to the Schlemm's canal, other than the hydrogel.

For some applications, introducing include injecting the liquid initiated solution.

For some applications, introducing includes introducing the liquid initiated solution at a single site of the Schlemm's canal.

For some applications, introducing includes introducing the liquid initiated solution into a plurality of segments of the Schlemm's canal at a respective plurality of sites along the Schlemm's canal.

For some applications, introducing the liquid initiated solution includes introducing at least 20 mm3 of the liquid initiated solution.

For some applications, introducing the liquid initiated solution includes introducing the liquid initiated solution at a pressure of at least 25 mmHg.

For some applications, the medical procedure is a first medical procedure, and the method further includes:
assessing a pressure in the eye at least 1 week following the first medical procedure; and
in response to assessing the pressure:
preparing a second liquid initiated solution by mixing at least third and fourth components;
during a second medical procedure, facilitating chemical transformation of the second liquid initiated solution to a second flexible semi-solid in the Schlemm's canal, by introducing the second liquid initiated solution into the Schlemm's canal within three hours of mixing; and
leaving the second flexible semi-solid in the Schlemm's canal upon conclusion of the medical procedure.

For some applications, introducing the first liquid initiated solution during the first medical procedure includes filling less than 75% of the Schlemm's canal with the first liquid initiated solution. For some applications, introducing the second liquid initiated solution during the second medical procedure includes filling at least part of a portion of the Schlemm's canal that was not filled with the first liquid initiated solution during the first medical procedure.

For some applications:
the medical procedure is a first test medical procedure,
the hydrogel is a first test hydrogel,
the liquid initiated solution is a first test initiated solution that is configured such that the first test hydrogel degrades less than four months after the conclusion of the first test medical procedure, and
the method further includes:
at least one month after the conclusion of the first test medical procedure, assessing an effectiveness of the first test hydrogel at increasing the aqueous outflow of fluid; and
if the first test hydrogel is effective at increasing the aqueous outflow of fluid:
preparing a second liquid initiated solution by mixing at least third and fourth components;
during a second medical procedure, facilitating chemical transformation of the second liquid initiated solution to a second flexible semi-solid in the Schlemm's canal, by introducing the second liquid initiated solution into the Schlemm's canal within three hours of mixing; and
leaving the second hydrogel in the Schlemm's canal upon conclusion of the second medical procedure, wherein the second initiated solution is configured such that the second hydrogel does not degrade until at least two years after the conclusion of the second medical procedure.

For some applications, one of the third and the fourth components includes ammonium persulfate (APS).

There is additionally provided, in accordance with an application of the present invention, a method for increasing the aqueous outflow of fluid through a trabecular meshwork and into a Schlemm's canal of an eye, the method including:

introducing a liquid precursor solution into the Schlemm's canal, during a medical procedure;

transforming the liquid precursor solution to form a water-permeable flexible semi-solid in the Schlemm's canal, during the medical procedure; and leaving the semi-solid in the Schlemm's canal upon conclusion of the medical procedure.

For some applications, transforming the liquid precursor solution includes polymerizing the liquid hydrogel precursor solution to form a water-permeable flexible semi-solid hydrogel in the Schlemm's canal, during the medical procedure.

For some applications, introducing the liquid precursor solution includes introducing at least 20 mm3 of the liquid precursor solution. For some applications, introducing the liquid precursor solution includes introducing the liquid precursor solution at a pressure of at least 25 mmHg.

There is yet additionally provided, in accordance with an application of the present invention, a method for increasing the aqueous outflow of fluid through a trabecular meshwork and into a Schlemm's canal of an eye, the method including:

introducing a first liquid hydrogel precursor solution into the Schlemm's canal, during a medical procedure;

introducing a second liquid hydrogel precursor solution into the Schlemm's canal, during the medical procedure, wherein the first and the second liquid hydrogel precursor solutions are different from each other, and are configured to together form a water-permeable flexible semi-solid hydrogel in the Schlemm's canal, during the medical procedure; and leaving the hydrogel in the Schlemm's canal upon conclusion of the medical procedure.

For some applications, the first and the second liquid hydrogel precursor solutions are configured to together polymerize to form the water-permeable flexible semi-solid hydrogel in the Schlemm's canal.

For some applications, introducing the first and the second liquid hydrogel precursor solutions includes introducing at least 20 mm3 of the first and the second liquid hydrogel precursor solutions in aggregate. For some applications, introducing the first and the second liquid hydrogel precursor solutions includes introducing at least one of the first and the second liquid hydrogel precursors solution at a pressure of at least 25 mmHg.

The present invention will be more fully understood from the following detailed description of embodiments thereof, taken together with the drawings, in which:

BRIEF DESCRIPTION OF THE DRAWINGS

FIG. 2 is a schematic illustration of a technique for introducing a liquid hydrogel precursor solution into the Schlemm's canal, in accordance with some applications of the present invention.

DETAILED DESCRIPTION OF APPLICATIONS

FIGS. 1A-D are schematic illustrations of methods for increasing the aqueous outflow of fluid through a trabecular meshwork and into a Schlemm's canal 10 of an eye 12, in accordance with some applications of the present invention. The methods are used to treat glaucoma, typically by dilating and/or stretching the canal and/or the trabecular meshwork on a long-term basis. For some applications, the methods apply a force to the inner wall of the canal and the trabecular meshwork, in order to increase fluid permeability of the inner wall of the canal and/or reduce the outflow resistance of the trabecular meshwork, thereby increasing aqueous outflow through the normal trabeculocanalicular pathway. As a result, intraocular pressure is reduced to treat glaucoma.

Figure 1A:
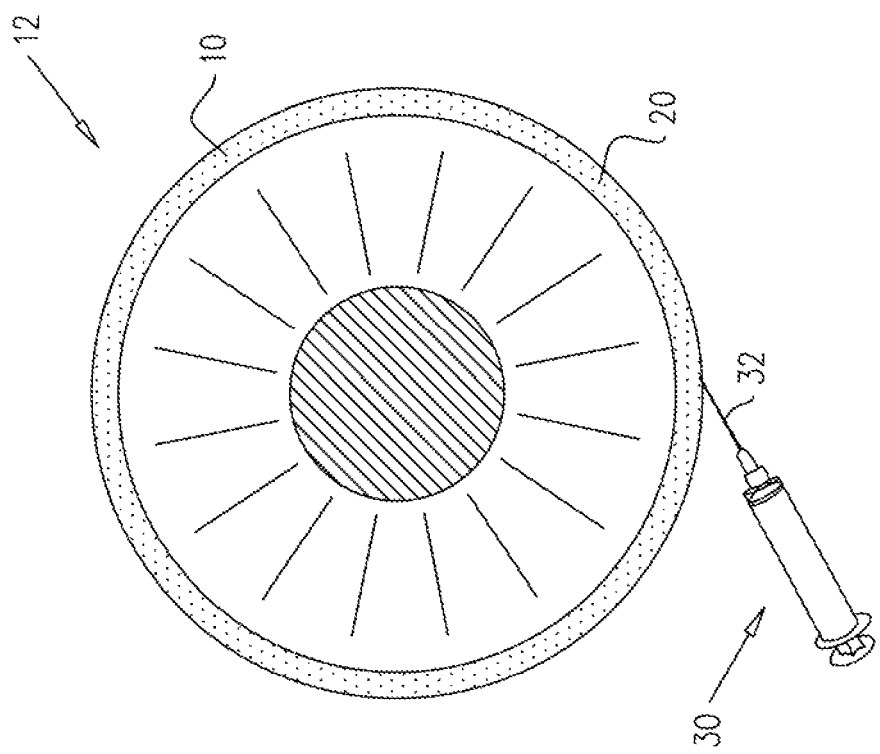
FIGS. 1A-D are schematic illustrations of methods for increasing the aqueous outflow of fluid through a trabecular meshwork and into a Schlemm's canal of an eye, in accordance with some applications of the present invention.
Figure 1B:
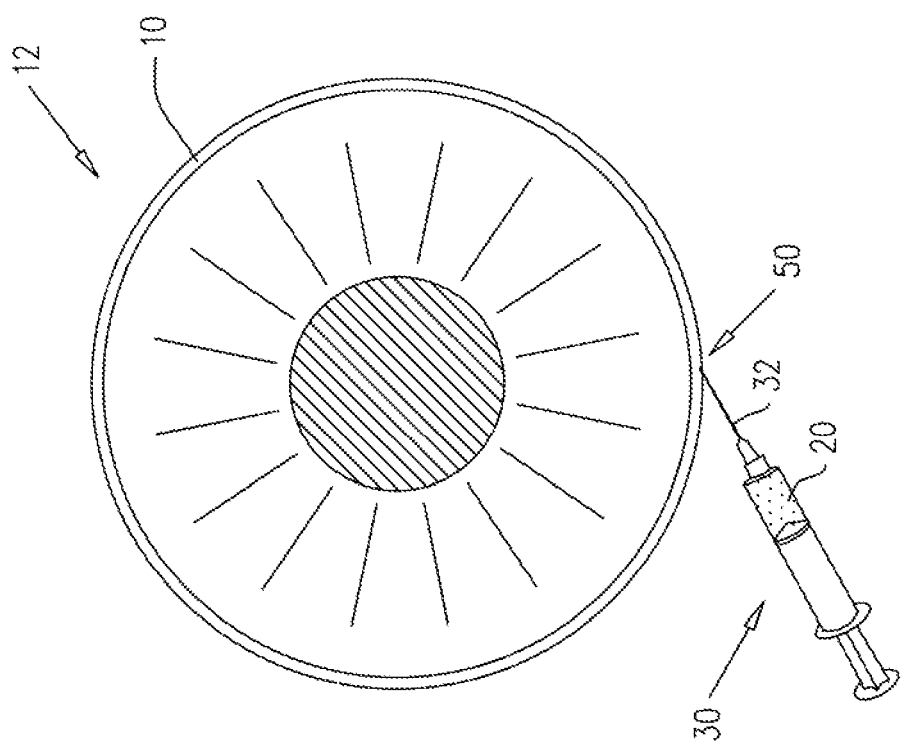
Figure 1D:
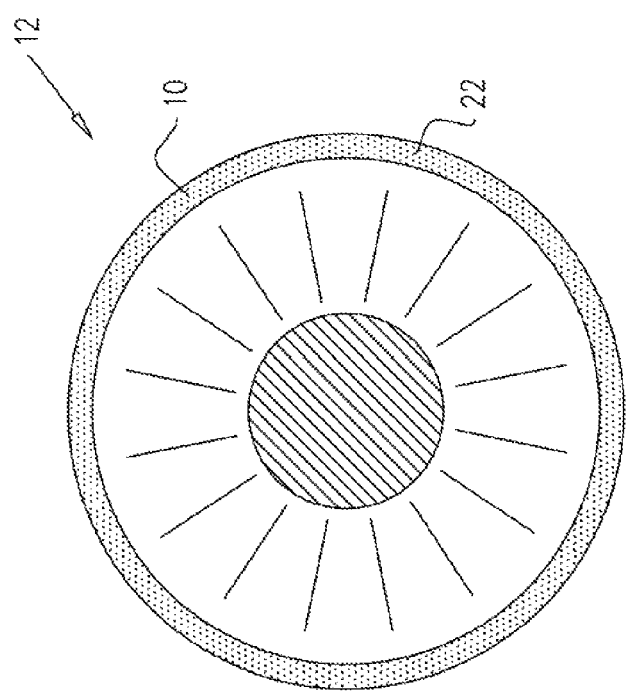
Figure 1C:
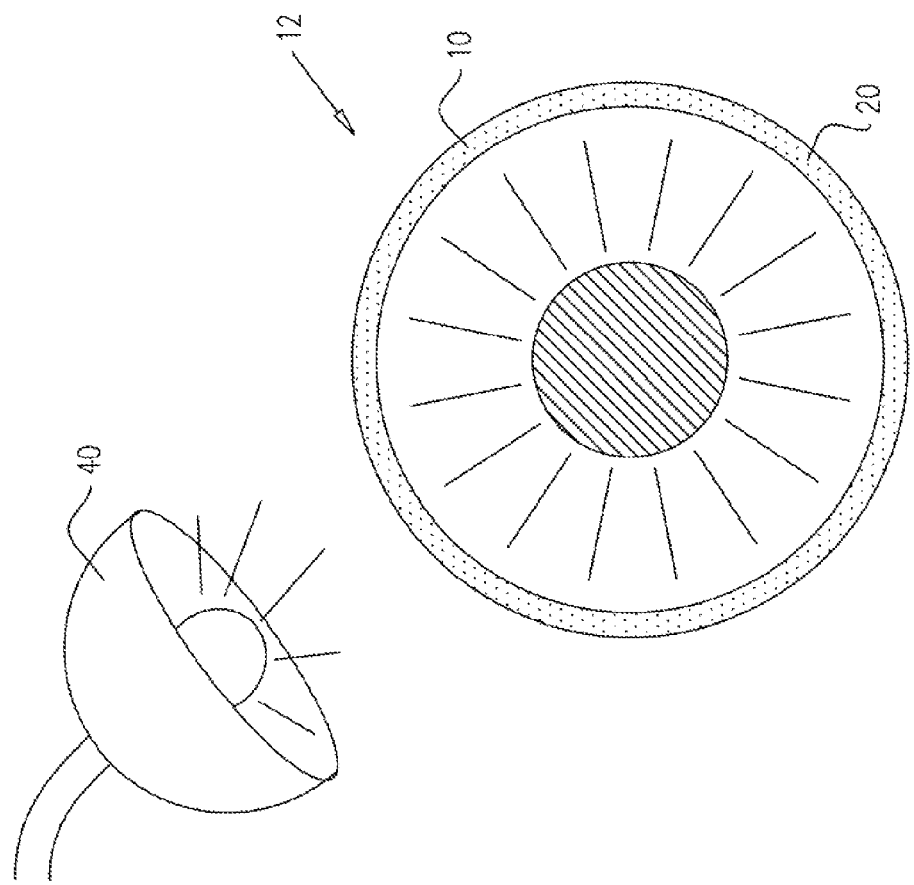

In some applications of the present invention, the methods comprise:

introducing a liquid hydrogel precursor solution 20 into Schlemm's canal 10, such as shown in FIGS. 1A-B, during a medical procedure;

crosslinking liquid hydrogel precursor solution to form a water-permeable flexible semi-solid hydrogel 22 in Schlemm's canal 10, such as shown in FIGS. 1C-D, during the medical procedure; and leaving hydrogel 22 in Schlemm's canal 10 upon conclusion of the medical procedure.

Because flexible semi-solid hydrogel 22 is highly water-permeable, it does not interfere with the desired flow in Schlemm's canal 10. Hydrogel 22 is left implanted in the canal on a long-term basis (e.g., at least one month, typically at least 6 months, such as at least two years, or indefinitely (although the hydrogel may eventually break down, after months or years). Hydrogel 22 thus maintains the patency of the canal on a long-term basis, thereby increasing the aqueous outflow of fluid through the canal. Hydrogel 22 thus serves as an implant. Typically, introducing liquid hydrogel precursor solution 20 comprises introducing at least 20 mm3 of the liquid hydrogel precursor solution, such as at least 30 mm3, e.g., 36 mm3, for applications in which the entire canal is filled.

Typically, introducing liquid hydrogel precursor solution 20 comprises using liquid hydrogel precursor solution 20 to dilate Schlemm's canal 10 (by applying fluid pressure to the wall of the canal). Typically, liquid hydrogel precursor solution 20 is introduced (e.g., injected) at a pressure of at least 25 mmHg, such as at least 30 mmHg. Because hydrogel precursor solution 20 is a liquid, it generally readily spreads through and fills the Schlemm's canal (or segments thereof, as described hereinbelow with reference to FIG. 2), without the need to separately dilate the canal, such as using an implant (e.g., a stent) and/or a viscoelastic. Inserting an implant and/or a viscoelastic generally requires creating a scleral flap and/or advancing a catheter through the entire length of the canal, which can be invasive and time-consuming.

For some applications, introducing liquid hydrogel precursor solution 20 comprises injecting the precursor solution, such as through a needle 32, such as a syringe (for such applications, the procedure might be considered "injection canaloplasty"). For some applications, needle 32 is inserted into the canal, such as using ultrasound imaging, without the need to create a scleral flap. Alternatively, the surgeon creates a scleral flap, and introduces the precursor solution via the flap. For some applications, liquid hydrogel precursor solution 20 has low viscosity, while for other applications, the precursor solution is viscous, such as slightly viscous. Needle 32 is removed from the Schlemm's canal after introducing liquid hydrogel precursor solution 20 through the needle, leaving the hydrogel in the Schlemm's canal.

Typically, liquid hydrogel precursor solution 20 comprises one or more polymerizable monomers and/or one or more polymerizable oligomers. For some applications, liquid hydrogel precursor solution 20 comprises one of the following materials, or a combination of two or more of the following materials:
- poly(ethylene glycol) (PEG), such as polyethylene (glycol) diacrylate (PEGDA) or PEG dimethacrylate (PEGDMA);
- alginate;
- agarose;
- chitosan; and/or
- collagen.

(PEG is a hydrophilic polymer that, when crosslinked into networks, can have a high water content. PEG is a suitable material for biological applications because it does not generally elicit an immune response. PEG hydrogels are chemically well-defined, and multiple chemistries can be used both for their formation and chemical modification.)

For some applications, liquid hydrogel precursor solution 20 is crosslinked by applying radiation to liquid hydrogel precursor solution 20 in Schlemm's canal (i.e., by photopolymerization, also known in the art as radiation curing). For example, as shown in FIG. 1C, a radiation source 40 may be used to apply the radiation. For example, the radiation may comprise ultraviolet (UV) radiation, infrared (IR) radiation (such as near-infrared (NIR) radiation), or electron-beam (EB) radiation. For some applications, liquid hydrogel precursor solution 20 is crosslinked by two-photon excitation. As known in the photopolymerization art, in two-photon excitation, two photons having a lower energy than UV (typically about twice the wavelength of UV) are focused onto individual molecules of the precursor solution, typically using scanning to polymerize a substantial volume of the solution. For example, the photons may be generated using a microscope, such as a laser scanning microscope. The photons generally penetrate tissue well, and thus can be applied from outside the body, such as through the sclera. (See, for example, Sun H-B et al., "Two-photon photopolymerization and 3D lithographic microfabrication," Adv. Polym. Sci. 170, 169-273 (2004), which is incorporated herein by reference. In case of conflict between the definitions used herein and those used in the Sun et al. paper, the definitions used herein shall control.) For some applications, liquid hydrogel precursor solution 20 comprises one or more of the materials listed above, and/or other materials, and is cured by one of the types of radiation listed above.

For some applications, radiation source 40 is be disposed outside of eye 12, and generates the radiation at an intensity that is sufficient to penetrate the sclera to Schlemm's canal 10. (Although radiation source 40 is shown off to the side in FIG. 1C, this is merely schematic; in practice, the radiation source is typically held directly in front of eye 12.) In particular, IR radiation readily penetrates the sclera, but other radiation, such as UV and EB radiation, also penetrate the sclera. Alternatively, a light beacon may be incorporated into an elongated tool, which is advanced through the Schlemm's canal after liquid hydrogel precursor solution 20 has been introduced into the canal.

For some applications, liquid hydrogel precursor solution 20 further comprises a photoinitiator. For some applications, the radiation interacts with the light-sensitive photoinitiator to create free radicals that initiate polymerization to form crosslinked hydrogel 22. Such photopolymerization typically has a fast curing rate (between less than a second to a few minutes) at physiological temperatures, and produces minimal heat.

For example, liquid hydrogel precursor solution 20 may comprise:
- PEGDA dissolved in degassed and deionized water, and a photoinitiator, which is crosslinked by exposure to UV radiation. For example, liquid hydrogel precursor solution 20 may comprise PEGDA dissolved in DG Water and PEGcure Photoinitiator (all distributed by Glycosan, a division of BioTime, Inc., Alameda, Calif., USA), which is crosslinked by exposure to UV light at a wavelength 365 nm, for 15 minutes. Alternatively, liquid hydrogel precursor solution 20 may comprise PEGDA, which is crosslinked by exposure to IR (e.g., NIR) radiation or EB radiation;
- alginate and a photoinitiator, which is crosslinked by exposure to UV, IR (e.g., NIR), or EB radiation, or by two-photon excitation;
- agarose and a photoinitiator, which is crosslinked by exposure to UV, IR (e.g., NIR), or EB radiation, or by two-photon excitation;
- chitosan and a photoinitiator, which is crosslinked by exposure to UV, IR (e.g., NIR), or EB radiation, or by two-photon excitation;
- collagen and a photoinitiator, which is crosslinked by exposure to UV, IR (e.g., NIR), or EB radiation, or by two-photon excitation; and/or
- one or more of the UV-curable precursor solutions described in a paper by Farbod K, entitled, "UV and spontaneously cured polyethylene glycol-based hydrogels for soft and hard tissue scaffolds," Royal Institute of Technology, Stockholm 2010, which is incorporated herein by reference.

For some applications, at least two of the components of liquid hydrogel precursor solution 20 are combined outside of eye 12, before introducing precursor solution 20 into the Schlemm's canal; for example, precursor solution 20 may be introduced into the Schlemm's canal within three hours (such as within ten minutes, e.g., within three minutes) of combining the at least two of the components (liquid hydrogel precursor solution 20 is formulated to provide a reasonable amount of time for the surgeon to inject the solution before the solution begins to undergo substantial crosslinking). For example, one of the components may be a photoinitiator and the other component the other elements of solution 20 (e.g., one of the materials listed above dissolved in water, which typically comprise monomers and/or oligomers). For other applications, two or more of the components of precursor solution 20 are separately introduced into the canal, such as to prevent premature crosslinking before introduction into the canal. For example, one of the components may comprise a photoinitiator, and the other of the components the other constituents of precursor solution 20, which may comprise, for example, PEGDA, alginate, agarose, chitosan, and/or collagen dissolved in water. After (or while) the components mix in the canal, the radiation is applied to crosslink the precursor solution.

For some applications, liquid hydrogel precursor solution 20 comprises two components, one of which comprises a photoinitiator. For some applications, introducing liquid hydrogel precursor solution 20 comprises introducing one of the two components into the Schlemm's canal, and thereafter introducing the other of the two components into the Schlemm's canal. Alternatively, for some applications, introducing liquid hydrogel precursor solution 20 comprises mixing the two components while introducing them into the Schlemm's canal. Further alternatively, for some applications, before introducing liquid hydrogel precursor solution 20, the liquid hydrogel precursor solution is prepared by mixing at least the two components, and introducing liquid hydrogel precursor solution 20 comprises introducing liquid hydrogel precursor solution 20 into the Schlemm's canal within three hours (such as within ten minutes, e.g., within three minutes) of mixing the at least the two components.

For some applications, liquid hydrogel precursor solution 20 is chemically crosslinked in Schlemm's canal (typically without applying radiation to liquid hydrogel precursor solution 20, other than any ambient light to which the solution may be exposed). For example, liquid hydrogel precursor solution 20 may be chemically crosslinked using a crosslinking agent, as known in the hydrogel art, which is introduced into Schlemm's canal 10 before, during, or after introducing liquid hydrogel precursor solution 20 into the canal. Alternatively, liquid hydrogel precursor solution 20 may be chemically crosslinked by changing a temperature and/or pH of the precursor solution, as is known in the hydrogel art.

For example, the crosslinking agent may comprise ammonium persulfate (APS), which produces free radicals that crosslink the polymerizable monomers and/or polymerizable oligomers of the liquid hydrogel precursor solution. For applications in which the liquid hydrogel precursor solution comprises PEG, the resulting hydrogel typically has a long life, i.e., does not degrade, e.g., for at least two years, such as indefinitely. Optionally, the crosslinking agent further comprises a co-initiator, such as ascorbic acid (AA). For example, techniques may be used, mutatis mutandis, that are described in an article by Shung A K et al., entitled, "Crosslinking characteristics of and cell adhesion to an injectable poly(propylene fumarate-co-ethylene glycol) hydrogel using a water-soluble crosslinking system," Tissue Eng. 2003 April; 9(2): 243-54, which is incorporated herein by reference. (In case of conflict between the definitions used herein and those used in the Shung et al. paper, the definitions used herein shall control.)

Alternatively, for example, liquid hydrogel precursor solution 20 may comprise thiol-modified hyaluronan, and the crosslinking agent may comprise a thiol-reactive crosslinking agent. For example, the thiol-modified hyaluronan may comprise Glycosil®, and the thiol-reactive crosslinking agent may comprise Extralink®-Lite (which comprises polyethylene glycol diacrylate) (both distributed by Glycosan).

Reference is still made to FIGS. 1A-D. As mentioned above, because hydrogel precursor solution 20 is liquid, it generally readily spreads through and fills the Schlemm's canal. Thus, for some medical procedures, in which precursor solution 20 fills the entire canal, it is sufficient to introduce liquid hydrogel precursor solution 20 at a single site 50 of Schlemm's canal 10, as shown in FIGS. 1A-B.

Reference is made to FIG. 2, which is a schematic illustration of a technique for introducing liquid hydrogel precursor solution 20 into Schlemm's canal 10, in accordance with some applications of the present invention. For some medical procedures, such as in which introducing hydrogel precursor solution 20 at a single site of the canal is insufficient to fill the entire canal, the surgeon introduces hydrogel precursor solution 20 into a plurality of segments 52 of the Schlemm's canal at a respective plurality of sites 50 along Schlemm's canal 10. For example, the segments may be disposed every 60, 90, or 120 degrees around the canal; in FIG. 2, four segments 52A, 52B, 52C, and 52D are shown disposed every 90 degrees around canal 10, and precursor solution is introduced at four sites 50A, 50B, 50C, and 50D. As a result, sometimes a complete, contiguous circle of precursor solution 20 (and, ultimately, hydrogel 22) is formed. Alternatively, a plurality of non-contiguous segments is formed, e.g., with stretching of the Schlemm's canal in the regions between the segments.

Whether liquid hydrogel precursor solution 20 is introduced into Schlemm's canal 10 at a single site 50 or a plurality of sites 50, liquid hydrogel precursor solution typically fills the canal along at least 50% of a circumference of the canal, such as at least 75%, e.g., 100% of the circumference of the canal (generally depending on the particular patient's anatomy). The liquid hydrogel precursor solution thus applies fluid pressure to the wall of the canal, typically along at least 50% of a circumference of the canal, such as at least 75%, e.g., 100% of the circumference of the canal, which dilates the canal.

Typically, upon crosslinking and/or polymerization of liquid hydrogel precursor solution 20 into hydrogel 22, hydrogel 22 is disposed (typically, filling) the canal along at least 50% of a circumference of the canal, such as at least 75%, e.g., 100% of the circumference of the canal (generally depending on the particular patient's anatomy). Hydrogel 22 applies a force to the wall (typically the inner wall) of the canal and the trabecular meshwork, in order to increase fluid permeability of the inner wall of the canal.

For some applications, the medical procedure in which a treatment described herein is practiced is the first of two or more medical procedures. In such a case, the surgeon typically assesses a parameter of the eye, such as a pressure in the eye, at least 1 week (e.g., at least one month) following the first medical procedure. For example, such an assessment may include considering whether there has been a sufficient decrease in intraocular pressure. In response to assessing the pressure and determining that there has not been a sufficient decrease, the surgeon may introduce a liquid hydrogel precursor solution into the Schlemm's canal, during a second medical procedure (e.g., at least one week, such as at least one month following the first medical procedure). The liquid hydrogel precursor solution is crosslinked to form a water-permeable flexible semi-solid hydrogel in the Schlemm's canal, during the second medical procedure, and this hydrogel is left in the Schlemm's canal upon conclusion of the second medical procedure.

In such cases, during the first medical procedure, typically less than 75% (e.g., 30-60%) of the Schlemm's canal is filled with the liquid hydrogel precursor solution. Correspondingly, during the second medical procedure, the surgeon fills at least part of the portion of the Schlemm's canal that was not filled with liquid hydrogel precursor solution during the first medical procedure. As appropriate, this procedure may be performed iteratively, during a plurality of procedures (e.g., two, three, or four or more procedures).

Reference is made to FIGS. 1A-D and 2. In some applications of the present invention, methods are provided for increasing the aqueous outflow of fluid through Schlemm's canal 10 of eye 12, the methods comprising:
  introducing a first liquid hydrogel precursor solution into Schlemm's canal 10, during a medical procedure;
  introducing a second liquid hydrogel precursor solution into Schlemm's canal 10, during the medical procedure, wherein the first and the second liquid hydrogel precursor solutions are different from each other, and are configured to together crosslink and/or polymerize to form a water-permeable flexible semi-solid hydrogel in Schlemm's canal 10, during the medical procedure; and
  leaving hydrogel 22 in Schlemm's canal 10 upon conclusion of the medical procedure.

Typically, the first liquid hydrogel precursor solution comprises one or more polymerizable monomers and/or one or more polymerizable oligomers, and the second liquid hydrogel precursor solution comprises one or more polymerizable monomers and/or one or more polymerizable oligomers.

For some applications, the first and the second liquid hydrogel precursor solutions are configured to together chemically crosslink and/or polymerize to form the hydrogel in the Schlemm's canal. For example, the first and the second liquid hydrogel precursor solutions may comprise the spontaneously-curable precursor solutions described in the above-mentioned paper by Farbod; for example, the first and the second liquid hydrogel precursor solutions may comprise one of the enes and one of the thiols, respectively, listed in Table 4 on p. 28 of the Farbod paper. (It is noted that the phrase "chemically crosslinking," as used in the present application, including in the claims, includes within its scope "spontaneously curing" by a chemical reaction, as used in the Farbod paper, as well as "physically curing" (by change in pH or temperature), as used in the Farbod paper. In case of conflict between the definitions used herein and those used in the Farbod paper, the definitions used herein shall control.) Alternatively, for example, the first liquid hydrogel precursor solution may comprise PEG (e.g., comprising PEGDA or PEG-DMA), and/or the second liquid hydrogel precursor solution may comprise ammonium persulfate (APS) (and, optionally, AA), as described hereinabove.

For some applications of these techniques, the crosslinking and/or polymerization occurs without applying radiation to the mixed first and second liquid hydrogel precursor solutions, other than any ambient light to which the solution may be exposed. Alternatively, radiation, such as UV, IR, or EB radiation is applied to the mixed solution while the solution is in the Schlemm's canal, or two-photon excitation is used, such as described hereinabove.

For some applications, at least one of the first and the second liquid hydrogel precursor solutions comprises a crosslinking agent. For some applications, a crosslinking agent is separately provided and/or introduced into the Schlemm's canal.

These techniques may be implemented with any of the techniques described hereinabove with reference to FIGS. 1A-D and 2.

Reference is again made to FIGS. 1A-D and 2. For any of the applications described hereinabove, crosslinking liquid hydrogel precursor solution 20 may optionally comprise:

observing a change in color of liquid hydrogel precursor solution 20 that is indicative of a level of crosslinking of the liquid hydrogel precursor solution; and terminating the crosslinking in response to the change in color.

In other words, the change in color is used as feedback to monitor the level of crosslinking (and formation of hydrogel). For example, techniques may be used, mutatis mutandis, that are described in an article by Poorsattar B M et al., entitled, "The effect of different curing time regimens on immediate postpolymerization color changes of resin composites," J Contemp Dent Pract. 1; 13(4):472-5 (July 2012), which is incorporated herein by reference. (In case of conflict between the definitions used herein and those used in the Poorsattar paper, the definitions used herein shall control.)

Reference is again made to FIGS. 1A-D and 2. In some applications of the present invention, methods are provided for increasing the aqueous outflow of fluid through Schlemm's canal 10 of eye 12, the methods comprising:

preparing liquid initiated solution by mixing at least first and second components, which initiates crosslinking;

during a medical procedure, facilitating chemical transformation (such as chemical crosslinking and/or chemical polymerization) of the liquid initiated solution to flexible semi-solid hydrogel 22 in Schlemm's canal 10, by introducing the liquid initiated solution into Schlemm's canal 10 within three hours (such as within ten minutes, e.g., within three minutes) of mixing; and leaving flexible semi-solid hydrogel 22 in Schlemm's canal 10 upon conclusion of the medical procedure.

In other words, unlike some the techniques described hereinabove, the present technique does not comprise the step of actively crosslinking and/or polymerizing liquid hydrogel precursor solution 20 in Schlemm's canal 10. Instead, the chemical crosslinking and/or polymerization is facilitated by introducing the liquid initiated solution soon after mixing, which initiates crosslinking and/or polymerization, and the crosslinking and/or polymerization is allowed to continue to occur in the canal after introduction. Because the liquid initiated solution is introduced into the canal soon after the mixing and the crosslinking and/or polymerization has begun, most of the crosslinking and/or polymerization occurs in the canal. The initiated solution is thus still liquid when introduced, which allows the solution to readily spread through and fills the Schlemm's canal, as described above.

For some applications, the first component comprises a liquid hydrogel precursor solution, and the second component comprises a crosslinking agent. The liquid hydrogel precursor solution typically comprises one or more polymerizable monomers and/or one or more polymerizable oligomers. For example, the liquid hydrogel precursor solution may comprise PEG (e.g., comprising PEGDA or PEG-DMA), alginate, agarose, chitosan, or collagen. Alternatively or additionally, for example, the crosslinking agent may comprise APS (and, optionally AA), such as described hereinabove.

For some applications, the first component comprises a first liquid hydrogel precursor solution, and the second component comprises a second liquid hydrogel precursor solution, such as described hereinabove. For some applications, at least one of the first and the second liquid hydrogel precursor solutions comprises a crosslinking agent. For some applications, a crosslinking agent is separately provided and/or introduced into the Schlemm's canal.

These pre-mixing techniques may be implemented with any of the techniques described hereinabove with reference to FIGS. 1A-D and 2.

Reference is made to FIGS. 1A-D and 2. Typically, in the techniques described herein, the methods comprise, upon the conclusion of the medical procedure, not leaving any solid elements in Schlemm's canal 10, including no stents, sutures, filaments, or metal. Alternatively or additionally, typically, in the techniques described herein, the methods comprise, upon the conclusion of the medical procedure, not leaving, in Schlemm's canal 10, any elements placed into the Schlemm's canal during the medical procedure that apply any force to Schlemm's canal 10, other than hydrogel 22.

Reference is still made to FIGS. 1A-D and 2. For some applications, the liquid hydrogel precursors solutions described herein, and thus the resulting hydrogel, comprise at least one glaucoma drug, such as any glaucoma drug currently known in the art or developed in the future. Typically, the hydrogel is configured to provide long-term sustained release of the drug. For example, the hydrogel may comprise PEG, as described hereinabove, which has excellent long-term sustained release properties. Thus, in these applications, a treatment modality is provided that combines the mechanical treatment provided by the hydrogel implant with drug therapy.

For example, the at least drug may be selected from the following drug families and/or drugs:
- a parasympathomimetic agonist, such as pilocarpine;
- an alpha 2-adrenergic agonist, such as apraclonidine or brimonidine;
- a beta-blocker, such as betaxolol, levobetaxolol, or timolol;
- a prostaglandin analog, such as bimatoprost, latanoprost, tafluprost, or travoprost; or
- a carbonic anhydrase inhibitor, such as acetazolamide, brinzolamide, or orzolamide.

Reference is still made to FIGS. 1A-D and 2. For some applications in which PEG is a component of the liquid hydrogel precursor solutions described herein, the PEG comprises ester chains, in order to control the rate of degradation of the resulting hydrogel. For example, the liquid hydrogel precursor solution may be configured (such as by including an appropriate concentration of ester chains) to degrade between one and two years after implantation. This obviates the need to remove the hydrogel, in case it is decided that it is no longer appropriate for a particular patient.

For some applications, the liquid hydrogel precursor solution is configured (such as by including an appropriate concentration of ester chains) such that the resulting hydrogel degrades in several months (e.g., in at least one month (e.g., at least two months), no more than four months (e.g., no more than three months), and/or between one (e.g., two) and four (e.g., three) months. The solution is introduced into the canal as a test implantation of the hydrogel. Between one (e.g., two) and four months (e.g., three months) after implanting the test hydrogel, the effectiveness of the hydrogel at treating the glaucoma (by reducing intraocular pressure, by increasing the aqueous outflow of fluid) is assessed. For example, the test hydrogel may be considered successful if the intraocular pressure is reduced by 2 mmHg, e.g., 5 mmHg. If it is ascertained that the hydrogel works well, another liquid hydrogel precursor solution, which is configured to have a long life without degradation (e.g., to not degrade until at least two years after implantation), is introduced into the canal. For example, the second liquid hydrogel precursor solution may comprise APS (and, optionally, AA), such as described hereinabove.

For some applications, the first and the second liquid hydrogel precursor solutions, and thus the resulting first and second hydrogels, have different pharmaceutical profiles, i.e., comprise different glaucoma drugs, e.g., the first for short-term implantation, and the second for long-term implantation. The first and the second drugs may comprise, for example, any of the drugs or families of drugs listed above. For example, the first drug may comprise a parasympathomimetic agonist, such as pilocarpine, and/or the second drug may comprise a beta-blocker, such as betaxolol, levobetaxolol, or timolol.

Although the techniques hereinabove have generally been described as crosslinking liquid hydrogel precursor solution 20 to form water-permeable flexible semi-solid hydrogel 22, some of the techniques more generally comprise a method for increasing the aqueous outflow of fluid through Schlemm's canal 10 of eye 12, the method comprising:
- introducing a liquid precursor solution into Schlemm's canal 10; and
- transforming the liquid precursor solution to form a water-permeable flexible semi-solid in Schlemm's canal 10.

Although the methods described herein have been generally described as including crosslinking liquid hydrogel precursor solution 20, the methods may more generally comprise polymerizing liquid hydrogel precursor solution 20, without necessarily crosslinking the liquid hydrogel precursor solution. Thus, for example, a method is provided for increasing the aqueous outflow of fluid through a Schlemm's canal of an eye, the method comprising: introducing a liquid hydrogel precursor solution into the Schlemm's canal, during a medical procedure; polymerizing the liquid hydrogel precursor solution to form a water-permeable flexible semi-solid hydrogel in the Schlemm's canal, during the medical procedure; and leaving the hydrogel in the Schlemm's canal upon conclusion of the medical procedure. In addition, for example, a method is provided for increasing the aqueous outflow of fluid through a Schlemm's canal of an eye, the method comprising: introducing a first liquid hydrogel precursor solution into the Schlemm's canal, during a medical procedure; introducing a second liquid hydrogel precursor solution into the Schlemm's canal, during the medical procedure, wherein the first and the second liquid hydrogel precursor solutions are different from each other, and are configured to together crosslink to form a water-permeable flexible semi-solid hydrogel in the Schlemm's canal, during the medical procedure; and leaving the hydrogel in the Schlemm's canal upon conclusion of the medical procedure. In addition, for example, a method is provided for increasing the aqueous outflow of fluid through a Schlemm's canal of an eye, the method comprising: preparing a liquid initiated solution by mixing at least first and second components; during a medical procedure, facilitating chemical polymerization of the liquid initiated solution to a flexible semi-solid in the Schlemm's canal, by introducing the liquid initiated solution into the Schlemm's canal within three hours of mixing; and leaving the flexible semi-solid in the Schlemm's canal upon conclusion of the medical procedure.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for increasing the aqueous outflow of fluid through a trabecular meshwork and into a Schlemm's canal of an eye, the method comprising:
- introducing a liquid hydrogel precursor solution into the Schlemm's canal, during a medical procedure;
- crosslinking the liquid hydrogel precursor solution to form a water-permeable flexible semi-solid hydrogel in the Schlemm's canal, during the medical procedure; and
- leaving the hydrogel in the Schlemm's canal upon conclusion of the medical procedure.

2. The method according to claim 1, wherein introducing the liquid hydrogel precursor solution comprises using the liquid hydrogel precursor solution to dilate the Schlemm's canal.

3. The method according to claim 1, wherein introducing the liquid hydrogel precursor solution comprises applying fluid pressure to a wall of the Schlemm's canal.

4. The method according to claim 3, wherein introducing the liquid hydrogel precursor solution comprises applying the fluid pressure to the wall of the Schlemm's canal along at least 50% of a circumference of the Schlemm's canal.

5. The method according to claim 1, wherein introducing the liquid hydrogel precursor solution comprises filling the Schlemm's canal along at least 50% of a circumference of the Schlemm's canal.

6. The method according to claim 1, wherein introducing the liquid hydrogel precursor solution comprises introducing at least 20 mm3 of the liquid hydrogel precursor solution.

7. The method according to claim 1, wherein introducing the liquid hydrogel precursor solution comprises introducing the liquid hydrogel precursor solution at a pressure of at least 25 mmHg.

8. The method according to claim 1, wherein the liquid hydrogel precursor solution comprises poly(ethylene glycol) (PEG).

9. The method according to claim 8, wherein the PEG comprises polyethylene (glycol) diacrylate (PEGDA).

10. The method according to claim 1, wherein the liquid hydrogel precursor solution is viscous, and wherein introducing comprises introducing the viscous liquid hydrogel precursor solution.

11. The method according to claim 1, wherein crosslinking the liquid hydrogel precursor solution comprises applying radiation to the liquid hydrogel precursor solution in the Schlemm's canal.

12. The method according to claim 11, wherein applying the radiation comprises applying the radiation through sclera of the eye.

13. The method according to claim 11, wherein applying the radiation comprises applying infrared (IR) radiation to the liquid hydrogel precursor solution in the Schlemm's canal.

14. The method according to claim 11, wherein applying the radiation comprises applying ultraviolet (UV) radiation to the liquid hydrogel precursor solution in the Schlemm's canal.

15. The method according to claim 1, wherein crosslinking the liquid hydrogel precursor solution comprises chemically crosslinking the liquid hydrogel precursor solution.

16. The method according to claim 1, wherein leaving the hydrogel in the Schlemm's canal upon conclusion of the medical procedure comprises leaving the hydrogel in the Schlemm's canal for at least one month.

17. The method according to claim 1,
wherein introducing comprises inserting a needle into the Schlemm's canal and introducing the liquid hydrogel precursor solution through the needle,
wherein the method further comprises removing the needle from the Schlemm's canal after introducing the liquid hydrogel precursor solution through the needle, and
wherein leaving the hydrogel in the Schlemm's canal upon conclusion of the medical procedure further comprises leaving the hydrogel in the Schlemm's canal after removing the needle from the Schlemm's canal.

18. The method according to claim 1, further comprising, upon the conclusion of the medical procedure, not leaving any solid elements in the Schlemm's canal.

19. The method according to claim 1, further comprising, upon the conclusion of the medical procedure, not leaving, in the Schlemm's canal, any elements placed into the Schlemm's canal during the medical procedure that apply any force to the Schlemm's canal, other than the hydrogel.

20. The method according to claim 1, wherein the medical procedure is a first medical procedure, and wherein the method further comprises:
assessing a pressure in the eye at least 1 week following the first medical procedure; and
in response to assessing the pressure:
introducing a second liquid hydrogel precursor solution into the Schlemm's canal, during a second medical procedure;
crosslinking the second liquid hydrogel precursor solution to form a second water-permeable flexible semi-solid hydrogel in the Schlemm's canal, during the second medical procedure; and
leaving the second hydrogel in the Schlemm's canal upon conclusion of the second medical procedure.

21. A method for increasing the aqueous outflow of fluid through a trabecular meshwork and into a Schlemm's canal of an eye, the method comprising:
introducing a first liquid hydrogel precursor solution into the Schlemm's canal, during a medical procedure;
introducing a second liquid hydrogel precursor solution into the Schlemm's canal, during the medical procedure, wherein the first and the second liquid hydrogel precursor solutions are different from each other, and are configured to together crosslink to form a water-permeable flexible semi-solid hydrogel in the Schlemm's canal, during the medical procedure; and
leaving the hydrogel in the Schlemm's canal upon conclusion of the medical procedure.

22. A method for increasing the aqueous outflow of fluid through a trabecular meshwork and into a Schlemm's canal of an eye, the method comprising:
introducing a liquid precursor solution into the Schlemm's canal, during a medical procedure;
transforming the liquid precursor solution to form a water-permeable flexible semi-solid in the Schlemm's canal, during the medical procedure; and
leaving the semi-solid in the Schlemm's canal upon conclusion of the medical procedure.

23. The method according to claim 22, wherein transforming the liquid precursor solution comprises polymerizing the liquid hydrogel precursor solution to form a water-permeable flexible semi-solid hydrogel in the Schlemm's canal, during the medical procedure.

* * * * *